(12) United States Patent
Lafosse et al.

(10) Patent No.: US 8,231,682 B2
(45) Date of Patent: Jul. 31, 2012

(54) INSTRUMENT FOR USE IN A JOINT REPLACEMENT PROCEDURE

(75) Inventors: Laurent Lafosse, Sevrier (FR); Julien Hee, Lyons (FR)

(73) Assignee: Depuy Ireland Limited, County Cork (IE)

(*) Notice: Subject to any disclaimer, the term of this patent is extended or adjusted under 35 U.S.C. 154(b) by 147 days.

(21) Appl. No.: 11/916,403

(22) PCT Filed: Jun. 2, 2006

(86) PCT No.: PCT/IB2006/002187
§ 371 (c)(1),
(2), (4) Date: Sep. 5, 2008

(87) PCT Pub. No.: WO2006/136954
PCT Pub. Date: Dec. 28, 2006

(65) Prior Publication Data
US 2009/0105837 A1  Apr. 23, 2009

(30) Foreign Application Priority Data

Jun. 3, 2005 (GB) .................................. 0511292.5
Feb. 22, 2006 (GB) .................................. 0603470.6

(51) Int. Cl.
*A61F 2/40* (2006.01)
(52) U.S. Cl. .................................. 623/19.11; 623/19.14
(58) Field of Classification Search .................. 606/89, 606/249
See application file for complete search history.

(56) References Cited

U.S. PATENT DOCUMENTS

| | | | |
|---|---|---|---|
| 5,070,623 A | 12/1991 | Barnes | |
| 5,364,401 A | 11/1994 | Ferrante | |
| 5,397,330 A | 3/1995 | Mikhail | |
| 5,462,549 A | 10/1995 | Glock | |
| 5,496,323 A | 3/1996 | Dye | |
| 5,514,139 A | 5/1996 | Goldstein | |
| 5,571,203 A | 11/1996 | Masini | |
| 5,683,397 A | 11/1997 | Vendrely | |
| 5,704,941 A | 1/1998 | Jacober | |
| 5,800,437 A | 9/1998 | Gustilo | |
| 6,197,063 B1* | 3/2001 | Dews | 623/19.14 |
| 6,203,575 B1* | 3/2001 | Farey | 623/18.11 |
| 6,258,097 B1 | 7/2001 | Cook | |
| 6,575,980 B1 | 6/2003 | Robie | |

(Continued)

FOREIGN PATENT DOCUMENTS

DE           10123517 C1    11/2002

(Continued)

OTHER PUBLICATIONS

PCT Written Opinion, 6 pages.

(Continued)

*Primary Examiner* — Eduardo C Robert
*Assistant Examiner* — Joshua Levine

(57) ABSTRACT

A trial implant component for use in a surgical procedure for replacement of a joint between a long bone and another bone, comprises a metaphyseal part which can be located so that it extends into a cavity at the resected face of the long bone in contact with the internal wall of the cavity in the metaphyseal region, and a disk which has an essentially flat shape and which can be fitted to the metaphyseal part to provide a gauge as to the appropriate size of a head part which is to be selected according to the location of the axis of the bone relative to the edge of the resected bone.

16 Claims, 2 Drawing Sheets

Standard Trial Head Disks

A:

Size 1   Size 2   Size 3   Size 4

Eccentric Trial Head Disks

B:

Size 2   Size 3   Size 4

U.S. PATENT DOCUMENTS

| | | |
|---|---|---|
| 6,589,282 B2 * | 7/2003 | Pearl .......................... 623/19.14 |
| 6,783,549 B1 | 8/2004 | Stone |
| 2002/0072805 A1 | 6/2002 | Sullivan |
| 2002/0099381 A1 | 7/2002 | Maroney |
| 2003/0114859 A1 | 6/2003 | Grusin |
| 2004/0064187 A1 | 4/2004 | Ball |
| 2004/0162619 A1 | 8/2004 | Blaylock |
| 2004/0186579 A1 | 9/2004 | Callaway |
| 2004/0215205 A1 | 10/2004 | Plumet |

FOREIGN PATENT DOCUMENTS

| | | | |
|---|---|---|---|
| EP | 0712617 | A1 | 5/1996 |
| EP | 0712617 | A | 9/1999 |
| EP | 1523964 | A | 4/2005 |
| EP | 1523964 | A2 | 4/2005 |
| FR | 2773469 | A | 7/1999 |
| FR | 2773469 | A1 | 7/1999 |
| FR | 2863859 | A1 | 6/2005 |
| GB | 1448111 | A | 9/1976 |
| WO | WO 94/15551 | A | 7/1994 |
| WO | WO 9415551 | A | 7/1994 |
| WO | WO 9636284 | A1 | 11/1996 |
| WO | WO 99/15084 | A1 | 4/1999 |
| WO | WO 9915084 | A1 | 4/1999 |
| WO | WO 02/17822 | A1 | 3/2002 |
| WO | WO 0217822 | A1 | 3/2002 |
| WO | WO 0226145 | A1 | 4/2002 |
| WO | WO 03094803 | A1 | 11/2003 |

OTHER PUBLICATIONS

International Search Report, dated Oct. 23, 2006, 5 pages.
UK Search Report, dated Oct. 4, 2005, 1 page.
UK Search Report, dated May 12, 2006, 1 page.
U.S. Appl. No. 11/916,415, filed Nov. 19, 2008; Non-Final Rejection May 14, 2010.

* cited by examiner

INSTRUMENT FOR USE IN A JOINT REPLACEMENT PROCEDURE

This invention relates to an instrument for use in a procedure for implanting an joint prosthesis in a joint between a long bone and another bone.

It is desirable that the areas of the bearing surfaces of components of a joint prosthesis are maximised in order to minimise localised stresses on the bearing surfaces. However, a patient's bone structures and the spaces between them can limit the available space for implanted components and can therefore restrict the size of components that can be used.

The humeral component of many shoulder joint prostheses includes a metaphyseal part which extends into the intramedullary cavity, and a head part at the proximal end of the metaphyseal part, facing the glenoid component. It is common for the stem and head parts to be provided as separate modular components, although they might be provided as a single piece. The head part of the humeral component will have a convex bearing surface when the shoulder prosthesis is an anatomic prosthesis, which will articulate against a glenoid component having concave bearing surface. The head part will have a concave bearing surface when the shoulder prosthesis is a reverse prosthesis, which will articulate against a glenoid component having convex bearing surface.

The head part will often be approximately circular when viewed along the axis of the humeral prosthesis at its proximal end. It will be preferred for the transverse dimension of the head part (which will be its diameter when it is circular) to be as big as possible to minimise localised stresses. However, it will generally be preferred for the head part not to overlap the edge of the resected humerus.

The present invention provides a trial implant component which can be used to aid selection of the head part of a joint prosthesis, which includes a flat disk which can be fitted to a metaphyseal part to provide a gauge as to the appropriate size of head part which is to be selected according to the location of the bone axis relative to the edge of the resected bone.

Accordingly, in one aspect, the invention provides a trial implant component for use in a surgical procedure for replacement of a joint between a long bone and another bone, which comprises a metaphyseal part which can be received in the intramedullary cavity of a long bone, and a disk which has an essentially flat shape and which can be fitted to the metaphyseal part to provide a gauge as to the appropriate size of a head part which is to be selected according to the location of the axis of the bone relative to the edge of the resected bone.

The use of a disk as a part of a trial implant component has the advantage that the location of the edge of the disk relative to the edge of the resected bone can be inspected more easily than if a trial head part (which might have the shape of part of a sphere when the joint prosthesis is an anatomic prosthesis) is used.

It will generally be preferred that the disk has openings extending through it, through which the resected bone can be inspected. This can assist a surgeon in assessing the size of the disk relative to the size of the bone. For example, the disk can have an outer rim, which might, for example, be approximately circular. Preferably, the rim is approximately planar. The disk can have a plurality of spokes (with openings between them) which extend inwardly from the rim, for example to a central hub at or close to which they are connected. The point or points at which spokes are connected to one another can define the hub.

It will generally be preferred for the disk and the metaphyseal part to be provided as modular components which can be assembled together. In this way, different disks can be fitted to a metaphyseal part while the metaphyseal part is implanted within the long bone, to assess the fit of the disks relative to the edge of the bone.

Accordingly, in another aspect, the invention provides a kit which includes a metaphyseal part and at least two of the disks, in which the configuration of one of the disks is different from the configuration of the other disk. For example, the disks might differ in terms of size. They might differ in terms of the location of a fixing feature (for example a spigot or a socket) relative to the edge of the disk (different eccentricities).

The metaphyseal part of the trial component of the invention can also be used with a trial head part, with a surface which corresponds to the bearing surface of the corresponding component of the implanted prosthesis component. Generally, the trial head part will be fitted to the metaphyseal part in a step which is performed after the disk has been used. It will generally be the case that the previous use of one or more disks in the selection of a trial head part will help to ensure that the head part is of an appropriate size, or at least close to the appropriate size, for the intended application. The bearing surface of the trial head part will generally be rounded. It can be convex when the trial implant component is a stem component of an anatomic joint prosthesis. It can be concave when the trial implant component is a stem component of a reversed joint.

The metaphyseal part of the trial implant component of the invention can have a superior plate which can sit on the resected long bone on the resection plane thereof. The plate might extend around the entire periphery of the metaphyseal part. However, it can frequently be appropriate for the plate to extend around less than all of the periphery of the metaphyseal part. For example, the plate might be provided at two or more spaced apart locations on the periphery of the metaphyseal part.

Preferably, the ratio of the length of the metaphyseal part measured between the superior and inferior faces along the assembly axis to its width at the superior face measured generally along the medial-lateral axis is not more than about 1.0, more preferably not more than about 0.7, especially not more than about 0.5.

Preferably, the metaphyseal part has a part of a spigot and socket assembly for engaging a mating component which has the corresponding part of the said assembly, the spigot and socket assembly defining an assembly axis, in which the length of the metaphyseal part measured along the assembly axis is not more than about 5 cm, more preferably not more than about 3 cm, especially not more than about 2 cm.

Preferably, the length of the metaphyseal part measured from the superior face to the inferior face parallel to the assembly axis is greater at the lateral edge than at the medial edge. For example, the ratio of the length of the metaphyseal part measured from the superior face to the inferior face parallel to the assembly axis at the lateral edge to the length at the medial edge is at least about 1.1, preferably at least about 1.25, for example at least about 1.4.

The use of a metaphyseal part in the trial implant component of the invention with features such as those mentioned above has the advantage that it can facilitate carrying out the joint replacement procedure through a small incision.

Preferably, one of the disk and the metaphyseal part carries a spigot and the other has a socket formed in it in which the spigot can be received. When the disk comprises spokes which are connected to one another at a hub, the spigot or the socket can be provided at the hub. It will generally be preferred for the spigot to be provided on the disk and for the socket to be formed in the metaphyseal part. The spigot and the socket should be configured so that the spigot is a snug fit in the socket. Frequently, the spigot and socket will have a tapered shape.

The spigot or socket (as the case might be) which is provided on the disk can be located centrally on the disk. However, it can often be preferred that the spigot or socket to be located eccentrically on the disk. In this way, the disk can be used in the selection of a head component which has a component of a spigot and socket assembly which is located off-centre, for example, for a situation where a surgeon is able to choose between head components with a range of eccentricities. The disk can also be used to determine the appropriate angular offset of a head component relative to the axis of the patient's bone, for example by being provided with markings on its rim which indicate the optimum angular offset.

The disk is made from polymeric material, selected from polyolefins, polyesters, poly-amides, polycarbonates and the like. The polymeric material can be reinforced by fibres. An advantage of using a polymeric material for the disk is that it can easily be made by a moulding process. Polymeric materials can also be relatively light weight. The use of polymeric materials gives a possible further advantage that disks of different sizes can be made easily with different colours for ease of identification and effective colour coding.

Metallic materials might also be used for the disk. Examples include such materials which are commonly used in the manufacture of surgical instruments, especially certain stainless steels.

Generally, the metaphyseal part will be formed from a metallic material. Preferred examples might include materials of the kind which are commonly used in the manufacture of surgical instruments, especially certain stainless steels.

The trial component of the present invention can be used as an aid to selection of components of joint prostheses for implantation in surgical procedures for replacement of joints which include the ankle joint, the knee joint, the hip joint, the elbow joint and the shoulder joint. It is particularly suitable for use in preparation of the femur to receive the femoral component of a hip joint prosthesis, and in preparation of the humerus to receive the humeral component of a shoulder joint prosthesis. The shape of the disk will depend on the intended application for the trial component. Its shape might be selected according to the shape of the surface of the part of the ultimate implant which faces towards the resected surface of the patient's bone. Its shape might be selected according to the shape of the resected surface of the patient's bone. A generally circular disk will be suitable for use in many shoulder joint applications. When the trial component is used as an aid to selection of the tibial component of a knee joint prosthesis, its shape might correspond to the shape of a resected tibia with a generally oval outline with the major axis running medial-lateral, having a notch in the posterior face.

The intended location of the metaphyseal part of the trial implant component can be determined as a result of pre-operative planning steps, in which the shape and size of the bone into which it is to be implanted are assessed by appropriate imaging techniques. Components of the trial implant component of the invention, including in particular the metaphyseal part or the disk or both and a trial head component if included, can be provided with features which enable its location (including orientation) to be tracked remotely, for example using opto-electronic or magnetic tracking apparatus. Such apparatus, and components which can be included in surgical instruments such as the trial implant component of the present invention are known. This can enable, for example, the height of the metaphyseal part relative to the resected surface of the humerus to be monitored. It can also enable the angular orientation of a disk which is not circular, or which is circular but with an eccentrically mounted fixing feature, to be monitored.

When the component of the invention is used in a procedure to replace a shoulder joint, the procedure can be performed through a supero-lateral incision. This technique avoids the need to release the subscapularis. It can therefore eliminate the risk of post-operative rupture of the subscapularis which can be associated with the known anterior approach through deltopectoral tissue. The use of the component in a procedure using a lateral approach is attractive because of the visibility of the resected surface of the humerus that is available through such an incision.

A further advantage of a shoulder joint procedure which is performed through a supero-lateral incision is that easier access to the glenoid is available compared with the known anterior approach through deltopectoral tissue, even when the size of the supero-lateral incision is small, and even taking account of surrounding soft tissue structures which might obstruct access to the joint space.

Preferably, the face of the metaphyseal part at its inferior end is approximately planar. It might be slightly rounded, especially at its peripheral edges.

Preferably, the ratio of the surface area of the metaphyseal part (excluding the ends of any ribs) at its superior face to the surface area at its inferior face is not more than about 3.0, more preferably not more than about 2.0. Preferably, the said ratio is at least about 1.3, more preferably at least about 1.5, for example at least about 1.75. When the superior face or the inferior face or either of them is not planar, the area that is measured is the projection of the face as defined by its peripheral edge. When the superior face has a socket formed in it, or a spigot extending from it, the area is again taken as the projection of the face as defined by its peripheral edge.

Preferably, the angle between the plane defined by the peripheral edge of the superior face of the metaphyseal part and the plane defined by the peripheral edge of its inferior face is at least about 5°, more preferably at least about 10°, for example at least about 15°. Preferably, the angle between the said planes is not more than about 50°, more preferably not more than about 35°, especially not more than about 30°.

Preferably, the metaphyseal part has a plurality of ribs extending along it which can be received in corresponding grooves in the internal wall of the long bone, to locate the metaphyseal part rotationally in the cavity.

Preferably, the trial implant component includes at least one rib on its side wall, preferably extending generally along the axis of the bone in which the trial implant component is to be used. The size and location of a groove which is formed in the internal wall of the bone can be arranged so that it can receive the or each corresponding rib on the joint prosthesis component which is to be implanted in the patient's bone. Ribs on the trial implant component correspond in size and position to ribs on the joint prosthesis component. On the joint prosthesis component, the ribs can be provided with openings extending through them which can receive sutures. The holes can then be used to anchor soft tissue to the prosthesis component.

The long bone can be prepared to receive the trial implant component of the invention a surgical procedure which includes the steps of:

making an incision, locating a plane on which to resect the long bone to remove the head, performing a resection to remove the head of the bone, preparing the cavity within the resected bone to receive the stem part of the trial implant component, and subsequently the implant component of the joint prosthesis, implanting the stem part of the trial implant component, fitting a disk to the stem part of the trial implant component to assess the proximity of the edge of a component of a final implant prosthesis to the edge of the resected bone, and replacing the disk with another disk which has a different configuration (for example size or eccentricity).

More particularly, it is preferred that the procedure includes the steps of:

using a trial disk to determine the relevant width of the resected bone so that an implant with an appropriate transverse size (which will be a diameter when the implant is circular) is selected, using a cutting guide to determine the height of the resected head of the bone so that an implant with the appropriate height is selected, and using a trial head component to assess soft tissue balance during articulation of the joint.

The surgical procedure will generally include a step of assembling the head and stem parts of a joint prosthesis component, after the appropriate head part has been selected. The head and stem parts can be fitted together using appropriately matching spigot and stem features, especially with matched tapering surfaces, as is well known. Care should be taken to match the eccentricity which is identified when using the trial disk in the eccentric arrangement of the head and stem parts of the component. This can be achieved conveniently using marks on the trial disk as points of reference.

The cavity within the long bone can be prepared using appropriate tools. Such tools might include drills, reamers, broaches and rasps, as is generally known.

In another aspect, the invention provides a method for a superolateral approach minimally invasive shoulder arthroplasty surgical procedure. The procedure can comprise some or all of the following: making an incision in the deltoid muscle along the direction of the deltoid fibres; splitting the deltoid muscle along its fibres; removing the glenohumeral ligaments and the coracoacromial ligament and releasing the biceps tendon; resecting the humeral head using a cutting guide; using a broach tool to provide a cavity within the humerus; using a trial stem inserted in the cavity to determine the size of a stem implant; using a trial head to determine the size of a head implant by engaging the trial head with a trial stem in the humerus; and implanting a stem implant and head implant having the determined sizes, and any combination thereof.

The incision is made in the direction along the deltoid fibres. Preferably, the incision is made substantially vertically. Preferably, the deltoid is split in the direction of the fibres and therefore the deltoid is not damaged during this procedure. After making an incision through the deltoid muscle a further incision is made through the cuff muscle. Preferably, the incision through the cuff muscle is made between the supraspinatus and the sub-scapularis. The present invention therefore has the advantage that the cuff muscles, in particular the subscapularis are not damaged during the procedure. The recovery time of the patient undergoing the surgical method of the present invention compared to the recovery time of a patient undergoing conventional methods can be significantly reduced.

Anatomic terms (such as superior, inferior, medial and lateral) are used in this document to refer to parts of the trial implant component of the invention, to distinguish different parts of the trial implant component from one another. The terms are applicable in the strict anatomic sense to parts of a trial implant component which is intended for use in shoulder replacement surgery. The terms can still be used to distinguish parts of a trial implant component from one another when they are not applicable anatomically, and in this case, the trial implant component should be envisaged with an appropriate rotational translation to relate it to a patient's anatomy.

Embodiments of the invention will now be described by way of example with reference to the accompanying drawings, in which.

Figure 1:
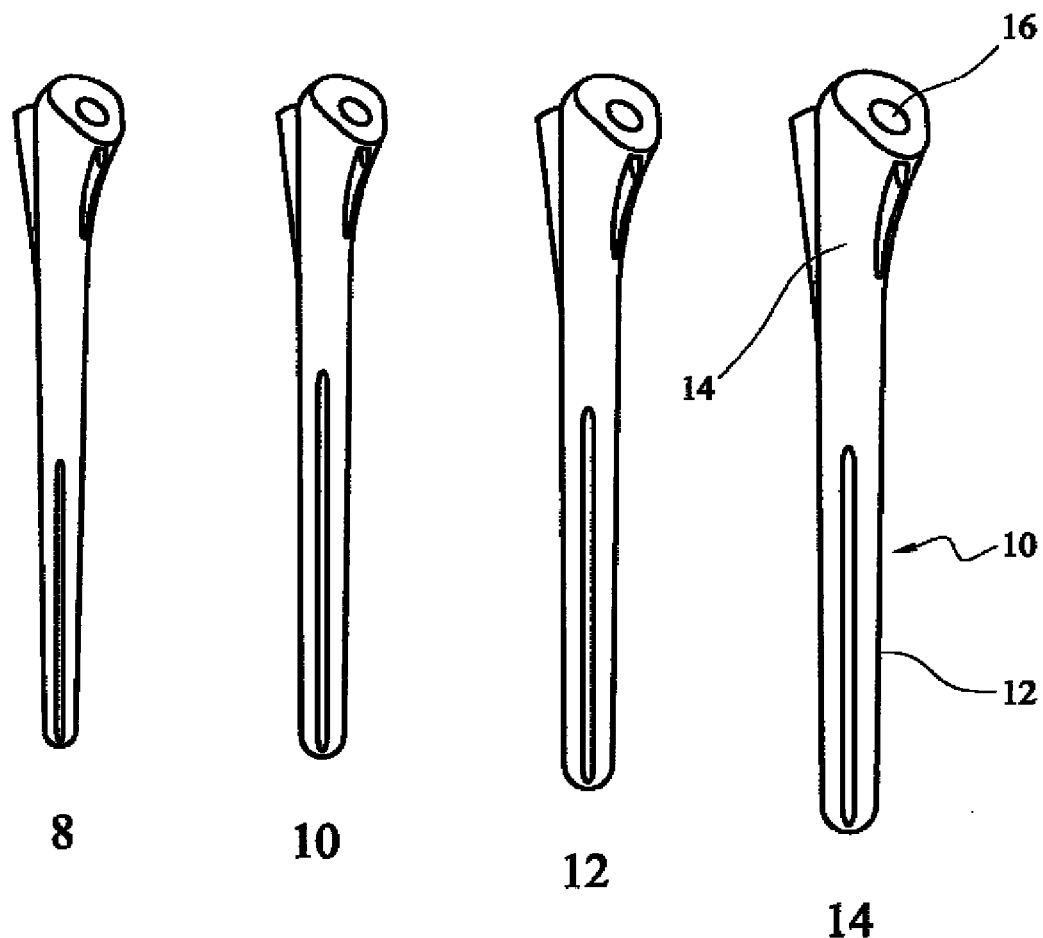
FIG. 1 is an isometric view of a conventional trial stem such as might have been used prior to the present invention in shoulder joint replacement surgery.

Referring to the drawings, FIG. 1 shows a conventional trial stem 10 which includes a distal stem part 12 and a proximal metaphyseal part 14. A plate 13 is provided on the superior face of the metaphyseal part extending from the medial and lateral edges thereof. An aperture 16 is provided in the superior face of the stem which can mate in use with a spigot on a trial head. The trial stem can be made of a polymeric material, such as an acetal resin.

The stem 10 is designed so that its shape closely corresponds to that of the implant component which ultimately is intended for implantation in a cavity within a patient's humerus, in particular in relation to its overall dimensions, both along the axis of the bone and in the plane which is perpendicular to that axis.

The trial stem which is shown in FIG. 1 has the disadvantage that it can be difficult to insert it into the intramedullary cavity in a bone through a small incision.

Figure 2:
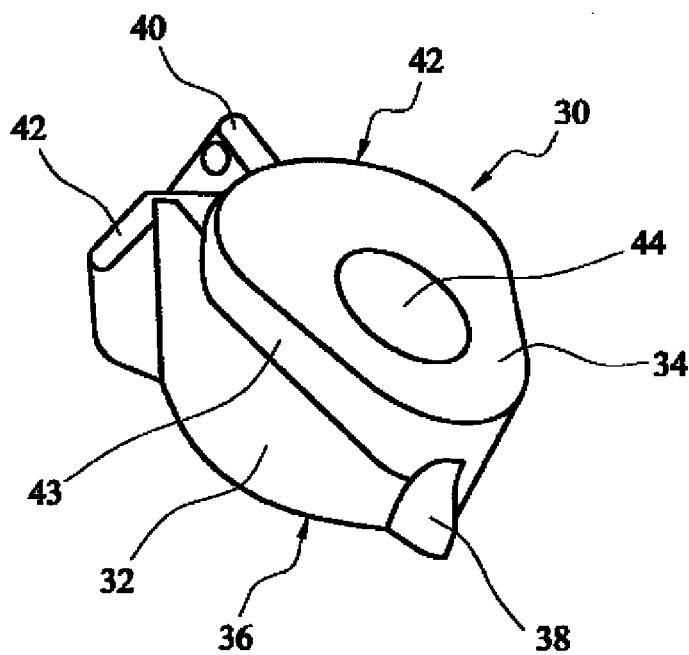
FIG. 2 is an isometric view of a trial implant component according to the present invention.

FIG. 2 shows a trial implant component 30 according to the invention. The trial implant component shown in FIG. 2 can be provided as part of a kit of components having differing sizes, as in the set shown in FIG. 1. The trial implant component 30 has a metaphyseal part 32 which can be located in a cavity at the resected face of a humerus or other long bone in contact with the internal wall of the cavity in the metaphyseal region. The metaphyseal part has a superior face 34 and an inferior face 36. A medial rib 38 is provided on the medially facing side of the metaphyseal part. A lateral rib 40 is provided on the laterally facing side of the metaphyseal part. First and second additional ribs 42 are provided on the laterally facing side of the metaphyseal part, one on each side of the lateral rib 40. The metaphyseal part has a plate 43 on its superior face which protrudes anteriorly and posteriorly beyond the portions of the metaphyseal part which extend into the bone cavity.

A tapering socket 44 is provided in the superior face of the metaphyseal part. The axis of the socket is perpendicular to the superior face.

The inferior face 36 of the metaphyseal part is planar and approximately parallel to the superior face.

The length of the metaphyseal part measured between the superior and inferior faces along the axis of the socket 44 is about 17 mm.

The width of the metaphyseal part at the superior face measured generally along the medial-lateral axis (not including any fin which extends from the superior face) is about 25 mm.

The ratio of the length of the metaphyseal part measured between the superior and inferior faces along the assembly axis to its width at the superior face measured generally along the medial-lateral axis is about 0.68.

The ratio of the surface area of the metaphyseal part at its superior face to the area at its inferior face is at least about 1.5, preferably at least about 1.75, for example about 2.0.

Figure 3:
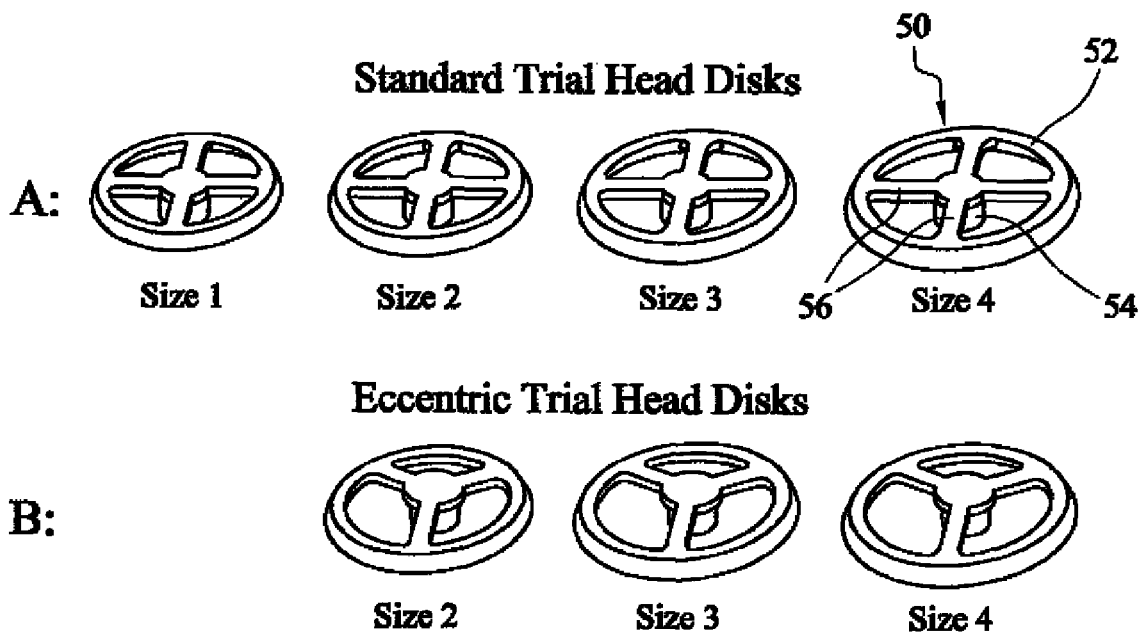
FIG. 3 is an isometric view of a trial disk.

FIG. 3 shows a set of trial disks which might be provided in a kit for use in a surgical procedure. The disks are provided in two subsets A, B. The disks in subset A have a hub which is located centrally relative to a rim. The disks in subset B have a hub which is located eccentrically relative to a rim. The disks within each subset differ from one another in size, so that the external diameters of the rim vary between 36 mm and 52 mm. The hub of each disk in subset B is offset from the centre of the rim by a distance of 4 mm.

Each trial disk 50 in the two subsets might be used with the trial implant component shown in FIG. 2. Each disk has a circular outer rim 52 which is generally planar. It includes a spigot 54 which is tapered along its length so that it is a snug fit in the socket 44 in the metaphyseal part. The spigot is connected to the rim by means of spokes 56. The spigot can be located centrally relative to the rim. The spigot can be located eccentrically relative to the rim.

A trial disk should be selected whose size is such that the rim of the disk does not overlap the edge of the resected bone. The size of the disk should preferably be such that the rim of the disk extends close to the edge of the bone.

Figure 4:
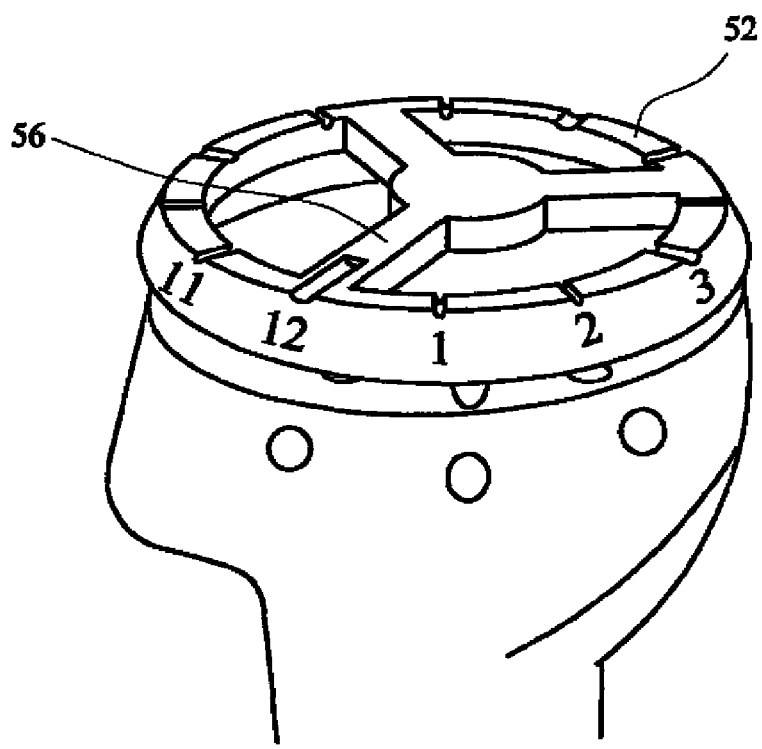
FIG. 4 is an isometric view of the trial implant component, with a trial disk, in place in the cavity within a resected humerus.

FIG. 4 shows an assembly of the metaphyseal part and the trial disk, with the meta-physeal part extending into in a cavity at the resected face of a humerus. The metaphyseal part of the assembly contacts the internal wall of the cavity in the metaphyseal region but does not extend further along the intramedullary cavity of the bone.

The disk is used to provide an indication of the radial extent of a humeral head which might be used with an implant component which is to be fitted into the cavity in the humerus. It is generally desirable to use a head which is as large as possible, consistent with the edge of the head not extending beyond the edge of the resected humerus. Different heads can be provided with different transverse dimensions, and different offsets between the spigot which is received in a socket in the stem component and the central axis of the head. The openings in the disk that are defined by the rim and the spokes allow the fit of the disk relative to the resected humerus to be assessed.

The invention claimed is:

1. A trial implant kit for use in a surgical procedure for replacement of a joint between a resected long bone and another bone, the resected long bone having an axis, an edge and a cavity formed therein, the cavity having an internal wall, comprising:
a metaphyseal part configured to be at least partially disposed within the cavity whereat a portion of the metaphyseal part is in contact with the internal wall; and
a first disk having a first outer rim defined by a first diameter and a plurality of spokes extending inwardly from the first outer rim connected to one another at a first hub, and a second disk having a second outer rim defined by a second diameter and a plurality of spokes extending inwardly from the second outer rim connected to one another at a second hub, the first disk and the second disks each having a substantially flat shape and being configured to be fitted to the metaphyseal part to provide a gauge as to the appropriate size of a head part which is to be selected according to the location of the axis of the bone relative to the edge, wherein the first hub is located substantially at the center of the first disk and the second hub is located at a position that is offset from the center of the second disk.

2. The trial implant kit of claim 1, wherein the first and second disks and the metaphyseal part are provided as modular components that can be assembled together.

3. The trial implant kit of claim 1, wherein the metaphyseal part has a superior surface and comprises one of a spigot that extends upwardly from the superior surface and a socket that is formed in the superior surface, and the first disk and the second disk each comprises one of a spigot that extends from the respective first hub and second hub and a socket formed in the respective first hub and second hub, in the respective first hub and second hub, and wherein the respective spigots are sized and shaped to be received in the respective sockets.

4. The trial implant kit of claim 3, wherein the spigot or socket of the first disk is located eccentrically relative to the center of the disk.

5. A trial implant kit of claim 1, wherein the first disk and the second disk have openings extending therethrough.

6. A trial implant kit of claim 1, wherein the first disk and the second disk are approximately circular.

7. The trial implant kit of claim 1, wherein the second hub is offset from the center of the second disk.

8. The trial implant kit of claim 7, wherein the second hub is offset approximately 4 mm from the center of the second disk.

9. A trial implant kit for use in a surgical procedure for replacement of a joint between a resected long bone and another bone, the resected long bone having an axis, an edge and a cavity formed therein, the cavity having an internal wall, comprising:
a metaphyseal part configured to be at least partially disposed within the cavity whereat a portion of the metaphyseal part is in contact with the internal wall; and
a first disk having a first outer rim defined by a first diameter and a plurality of spokes extending inwardly from the first outer rim connected to one another at a first hub located at a first position, and a second disk having a second outer rim defined by a second diameter and a plurality of spokes extending inwardly from the second outer rim connected to one another at a second hub located at a second position, the first disk and the second disks each having a substantially flat shape and being configured to be fitted to the metaphyseal part to provide a gauge as to the appropriate size of a head part which is to be selected according to the location of the axis of the bone relative to the edge of the resected bone, wherein the first diameter is greater than the second diameter.

10. The trial implant kit of claim 1, wherein the first and second disks and the metaphyseal part are provided as modular components that can be assembled together.

11. The trial implant kit of claim 1, wherein the metaphyseal part has a superior surface and comprises one of a spigot that extends upwardly from the superior surface and a socket that is formed in the superior surface, and the first disk and the second disk each comprises one of a spigot that extends from the respective first hub and second hub and a socket formed in the respective first hub and second hub, and wherein the respective spigots are sized and shaped to be received in the respective socket.

12. The trial implant kit of claim 3, wherein the spigot or socket of the first disk is located eccentrically relative to the center of the disk.

13. A trial implant kit of claim 1, wherein the first disk and the second disk have openings extending therethrough.

14. A trial implant kit of claim 1, wherein the first disk and the second disk are approximately circular.

15. The trial implant kit of claim 9, wherein the second hub is offset from the center of the second disk.

16. The trial implant kit of claim 15, wherein the second hub is offset approximately 4 mm from the center of the second disk.

* * * * *